United States Patent
Nishiyama et al.

(10) Patent No.: US 12,196,411 B2
(45) Date of Patent: Jan. 14, 2025

(54) LIGHT SOURCE DEVICE

(71) Applicant: STANLEY ELECTRIC CO., LTD., Tokyo (JP)

(72) Inventors: Rui Nishiyama, Tokyo (JP); Kenji Nagashima, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 18/595,181

(22) Filed: Mar. 4, 2024

(65) Prior Publication Data
US 2024/0310026 A1    Sep. 19, 2024

(30) Foreign Application Priority Data
Mar. 15, 2023  (JP) ................ 2023-040587

(51) Int. Cl.
| | |
|---|---|
| F21V 9/30 | (2018.01) |
| F21V 9/20 | (2018.01) |
| A61B 3/12 | (2006.01) |
| F21Y 113/20 | (2016.01) |
| F21Y 115/10 | (2016.01) |
| F21Y 115/30 | (2016.01) |

(52) U.S. Cl.
CPC ............. *F21V 9/30* (2018.02); *F21V 9/20* (2018.02); *A61B 3/1225* (2013.01); *F21Y 2113/20* (2016.08); *F21Y 2115/10* (2016.08); *F21Y 2115/30* (2016.08)

(58) Field of Classification Search
CPC . F21V 9/30; F21V 9/20; A61B 3/1225; F21Y 2113/20; F21Y 2115/10; F21Y 2115/30
See application file for complete search history.

(56) References Cited

U.S. PATENT DOCUMENTS

| | | | |
|---|---|---|---|
| 2009/0040754 A1* | 2/2009 | Brukilacchio | G02B 27/1006 362/228 |
| 2015/0105668 A1* | 4/2015 | Ehrhardt | G01N 21/6456 600/476 |
| 2016/0062103 A1* | 3/2016 | Yang | A61B 1/07 250/552 |
| 2020/0383558 A1* | 12/2020 | Goebel | G01J 3/108 |
| 2021/0124178 A1* | 4/2021 | Matsunobu | A61B 5/0071 |

FOREIGN PATENT DOCUMENTS

| | | |
|---|---|---|
| JP | 5681600 B2 | 3/2015 |
| JP | 2015171442 A | 10/2015 |

* cited by examiner

*Primary Examiner* — Evan P Dzierzynski
(74) *Attorney, Agent, or Firm* — Holtz, Holtz & Volek PC

(57) ABSTRACT

A light source device 10 includes a laser diode 12 configured to emit laser light LDb, a fluorescent body 18 configured to generate primary fluorescence FL1 from the laser light LDb, a notch filter 38 configured to generate secondary fluorescence FL2 from the primary fluorescence FL1, an LED 30 configured to emit LED light LEb, and a dichroic mirror 40 configured to combine the secondary fluorescence FL2 and the LED light LEb.

6 Claims, 5 Drawing Sheets

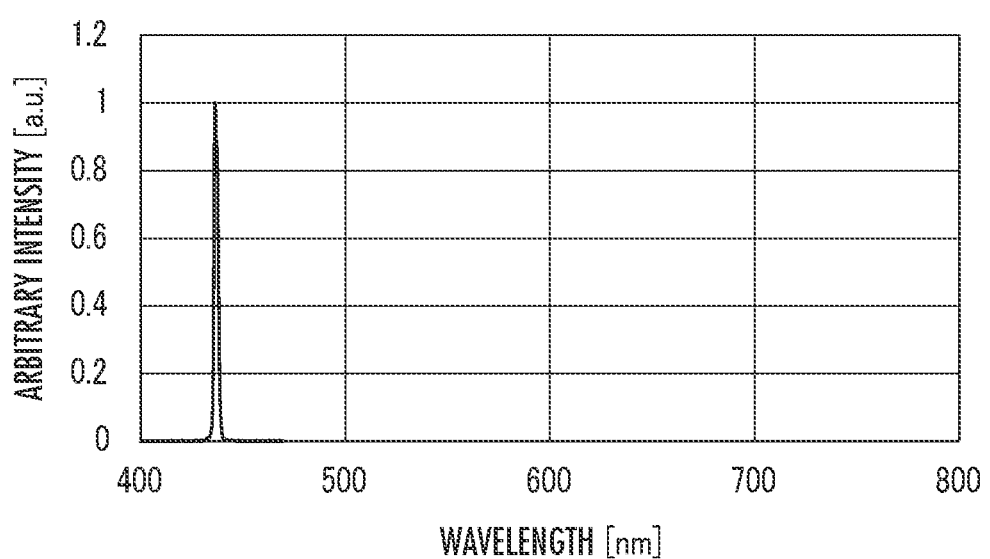

LIGHT SOURCE DEVICE

BACKGROUND OF THE INVENTION

1. Field of the Invention

The present invention relates to, for example, a light source device used for illumination of an imaging diagnostic device or the like.

2. Description of the Related Art

For example, illumination light used in imaging diagnosis with a fundus camera is desired to have a uniform intensity (light amount) in a predetermined wavelength range.

Japanese Patent Application Laid-Open No. 2015-171442 discloses a light source device for an endoscope. With this light source device, fluorescence and LED light are combined by a dichroic mirror, pass through a notch filter, and are then emitted.

Japanese Patent No. 5681600 discloses a biological particle evaluation device including a light source device that irradiates a particle to be measured. With the biological particle evaluation device, a part of laser light emitted from a laser light source of the light source device is branched as detection light at a detection point provided on the way of an optical path in order to detect a light amount of the laser light. The branched detection light is divided by a dichroic mirror after passing through a notch filter.

PRIOR ART DOCUMENTS

Patent Literature 1: Japanese Patent Application Laid-Open No. 2015-171442
Patent Literature 2: Japanese Patent No. 5681600

SUMMARY OF THE INVENTION

In the light source device of Japanese Patent Application Laid-Open No. 2015-171442, the fluorescence generated by the laser light and the LED light from an LED light source are first combined by the dichroic mirror, and then pass through the notch filter. Therefore, the intensity of the LED light source is significantly reduced, that is, insufficient, and the uniformity of the intensity of the combined light cannot be ensured in a sufficient wavelength range.

The dichroic mirror equipped in the light source device of Japanese Patent No. 5681600 is used for dividing light, instead of combining light. In a case where the dichroic mirror is disposed upstream of the notch filter in the optical path, two notch filters are required in total for processing of each divided light, and the cost is increased, so that the notch filter and the dichroic mirror are disposed in this order in the optical path of the light source device in order to avoid the increase in cost, and the reason is irrelevant to the uniformity of the intensity.

The light source devices of Japanese Patent Application Laid-Open No. 2015-171442 and Japanese Patent No. 5681600 are both equipped with the notch filter and the dichroic mirror separately. This configuration is disadvantageous in terms of size reduction and weight reduction of the light source device.

The present invention is to make a spectrum of a combined light of fluorescence generated by a laser light source and LED light uniform in a desired wavelength range in a light source device that emits the combined light.

An aspect of the present invention relates to a light source device including: a laser light source configured to emit laser light having a wavelength shorter than a first wavelength; a fluorescent body configured to emit primary fluorescence having a wavelength longer than the first wavelength in response to excitation by the laser light; a notch filter configured to emit secondary fluorescence obtained by attenuating the primary fluorescence from the fluorescent body in an attenuation wavelength range including a wavelength longer than the first wavelength; an LED light source configured to emit LED light having a wavelength shorter than the first wavelength; and a dichroic mirror configured to emit combined light obtained by combining the secondary fluorescence from the notch filter and the LED light from the LED light source.

According to the present invention, the fluorescence generated by the excitation of the laser light passes through the notch filter, is attenuated, and is then combined with the LED light in the dichroic mirror. As a result, it is possible to generate the secondary fluorescence in which the intensity is reduced from the primary fluorescence by the notch filter while avoiding a situation in which the intensity is insufficient due to the LED light passing through the notch filter, and to equalize the spectrum of the combined light with the wavelength range of the secondary fluorescence and the wavelength range of the LED light.

BRIEF DESCRIPTION OF THE DRAWINGS

FIG. 4E is a diagram showing a relationship between a wavelength and an arbitrary intensity of the laser light LDb emitted by the laser diode.

DESCRIPTION OF THE PREFERRED EMBODIMENTS

Figure 1:
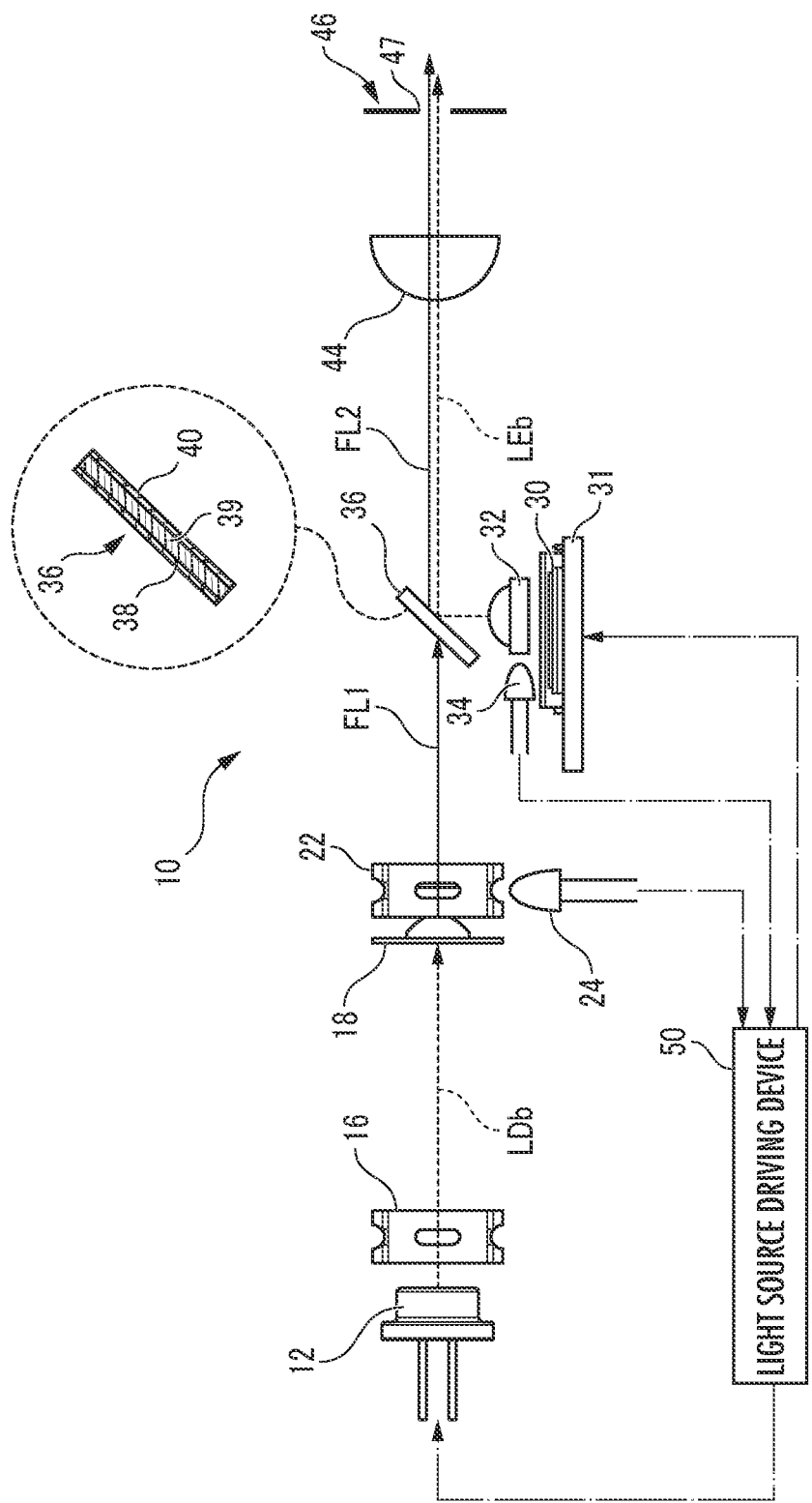
FIG. 1 is an overall view of a light source device used for imaging diagnosis with a fundus camera.

Hereinafter, an embodiment of the present invention will be described. It goes without saying that the present invention is not limited to the embodiment. The components common to a plurality of embodiments are denoted by the same reference numerals throughout the drawings.
(Configuration)

FIG. 1 is an overall view of a light source device 10 used for imaging diagnosis with a fundus camera. The light source device 10 according to the embodiment is used together with the fundus camera. The light source device 10 includes a laser diode 12 that emits blue laser light LDb and an LED 30 that emits blue LED light LEb. The laser light LDb is converted into primary fluorescence FL1 and secondary fluorescence FL2 in order. The combined wave of the secondary fluorescence FL2 and the LED light LEb is emitted to the outside from a slit 47 of a module case 46. Detailed characteristics of the laser light LDb, the LED light LEb, the primary fluorescence FL1, and the secondary fluorescence FL2 will be described with reference to FIGS. 2 and 3.

An optical axis of the laser diode 12 extends straight and penetrates the slit 47 of the module case 46. A collimator lens 16, a fluorescent body 18, a collimator lens 22, an optical element 36, and a collimator lens 44 are disposed in this order from the laser diode 12 toward the slit 47 along the optical axis. The LED 30 as a light source different from the laser diode 12 is mounted on an LED substrate 31. An optical axis of the LED 30 reaches the optical element 36, and the collimator lens 32 is disposed on an optical axis between the LED 30 and the optical element 36.

The optical element 36 includes a glass substrate 39, a notch filter 38 formed by film-formation on an incidence surface side of the primary fluorescence FL1 on the glass substrate 39, and a dichroic mirror 40 formed by film-formation on an incidence surface side of the LED light LEb on the glass substrate 39. The optical element 36 is disposed at an intersection of the two optical axes such that a normal line of a surface on the notch filter 38 side and a normal line of a surface on the dichroic mirror 40 side have an inclination angle of 45° with respect to the optical axis of the laser diode 12 and the optical axis of the LED 30, respectively.

A photodetector 24 detects an intensity of the primary fluorescence FL1 emitted from the collimator lens 22. Specifically, a hole is formed on a back surface side of the holder of the collimator lens 22 (an incidence surface and an emission surface of the collimator lens 22 are referred to as a front surface and a back surface, respectively), and the photodetector 24 is inserted into the hole to detect an intensity of the LED light LEb. Similarly, a photodetector 34 is also inserted into a hole on a back surface side of a holder of the collimator lens 32 to detect the intensity of the LED light LEb emitted from the collimator lens 32.

A light source driving device 50 controls driving voltages of the laser diode 12 and the LED 30 based on the outputs of the photodetectors 24 and 34. An intensity of the laser light LDb emitted by the laser diode 12 and the intensity of the LED light LEb emitted by the LED 30 are increased or decreased in response to the driving voltages of the laser diode 12 and the LED 30, respectively.

The notch filter 38 is disposed in a direction in which the primary fluorescence FL1 is incident at an incidence angle of 45°. As a result, in the primary fluorescence FL1, reflected light (reflected fluorescence FLc described later with reference to FIG. 2), which is not transmitted through the notch filter 38 and is reflected, is reflected on a side opposite to a disposition side of the photodetector 24 in a direction perpendicular to an optical axis of the primary fluorescence FL1.

Figure 2:
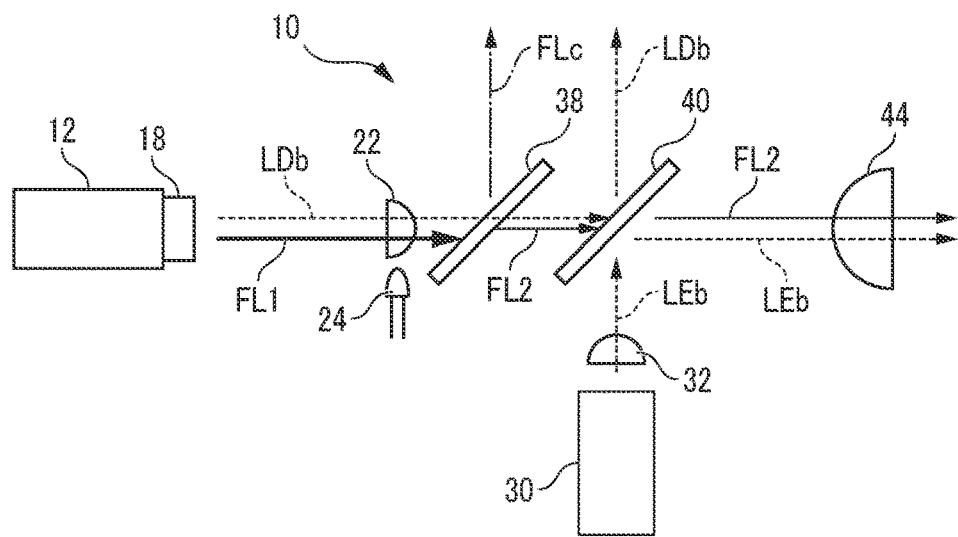
FIG. 2 is a view showing generation and flow of various types of light in a light source device.
Figure 3:
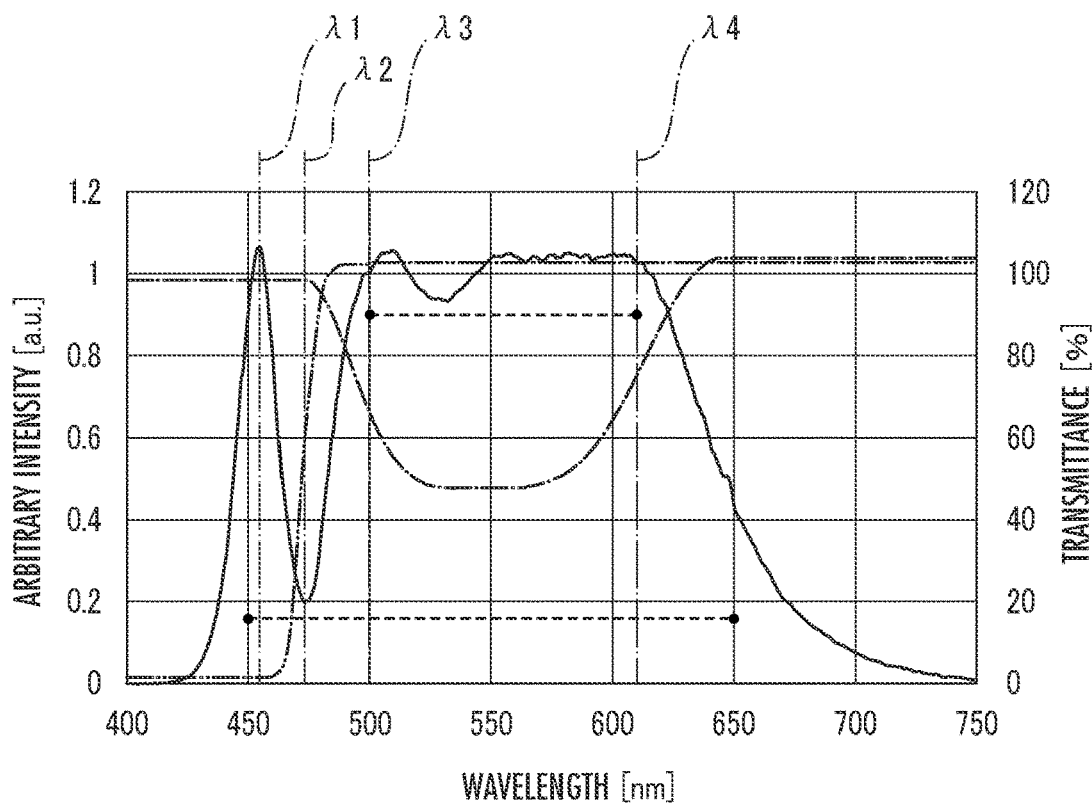
FIG. 3 is a diagram showing spectral characteristics of combined light or each element in the light source device.

FIG. 2 is a view showing generation and flow of various types of light in the light source device 10. FIG. 3 is a diagram showing spectral characteristics of combined light or each element in the light source device 10. In FIG. 3, wavelengths $\lambda 1$, $\lambda 2$, $\lambda 3$, and $\lambda 4$ are predetermined wavelengths (values), and $\lambda 1 < \lambda 2 < \lambda 3 < \lambda 4$. A solid line indicates a combined wave spectrum of the secondary fluorescence FL2 as the emitted light of the dichroic mirror 40 and the LED light LEb.

Target values are indicated by two broken lines, which are an upper broken line and a lower broken line. The upper broken line of the target value indicates the minimum intensity that should be ensured by a combined wave spectrum in a wavelength range of a wavelength $\lambda 3$ (for example, 500 nm) to a wavelength $\lambda 4$ (for example, 610 nm). The lower broken line of the target value indicates the minimum intensity that should be ensured by the combined wave spectrum outside a wavelength range of $\lambda 3$-$\lambda 4$. Further, a one-dot chain line and a two-dot chain line indicate characteristics of transmittances of the notch filter 38 and the dichroic mirror 40, respectively.

In FIG. 3, the wavelength $\lambda 1$ (for example, 460 nm) is a wavelength of the maximum intensity of the LED light LEb emitted by the LED 30. The wavelength $\lambda 2$ is a wavelength of the minimum intensity of the combined wave spectrum (for example, a wavelength of 470 nm to 480 nm). A unit of the intensity in FIG. 3 is an arbitrary intensity (a.u.).

Figure 4A:
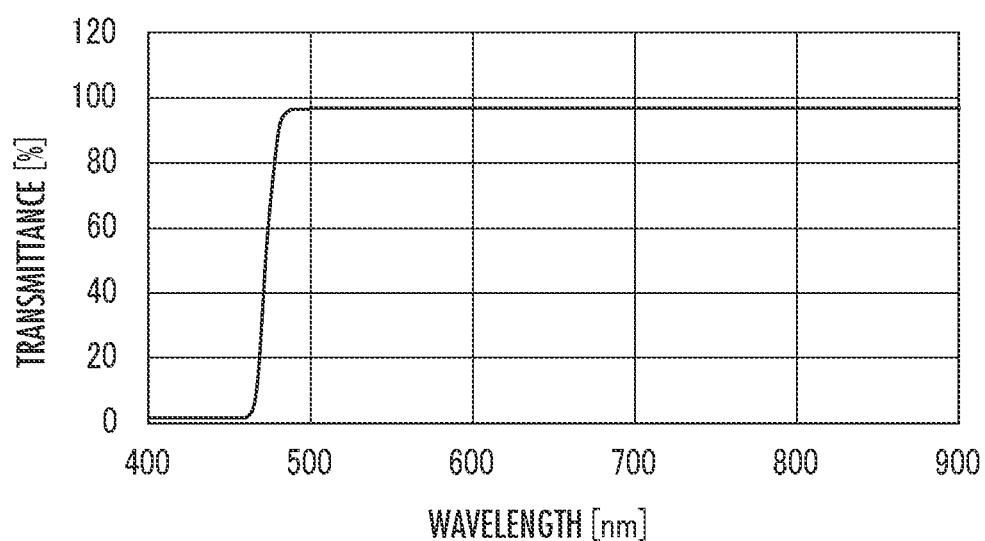
FIG. 4A is a diagram showing a relationship between a wavelength and a transmittance of a dichroic mirror.

FIGS. 4A to 4E will be described first. FIG. 4A is a diagram showing a relationship between the wavelength and the transmittance of the dichroic mirror 40. The characteristics of the transmittance of the dichroic mirror 40 are divided into a lower flat region having a short wavelength with a transmittance of substantially 0%, an upper flat region having a long wavelength with a transmittance of substantially 100%, and a rising region between both. The wavelength $\lambda 2$ in FIG. 3 corresponds to a wavelength (for example, a wavelength in a range of 470 nm to 480 nm) at a portion of substantially 3 db down from the upper flat region in the rising region.

Figure 4B:
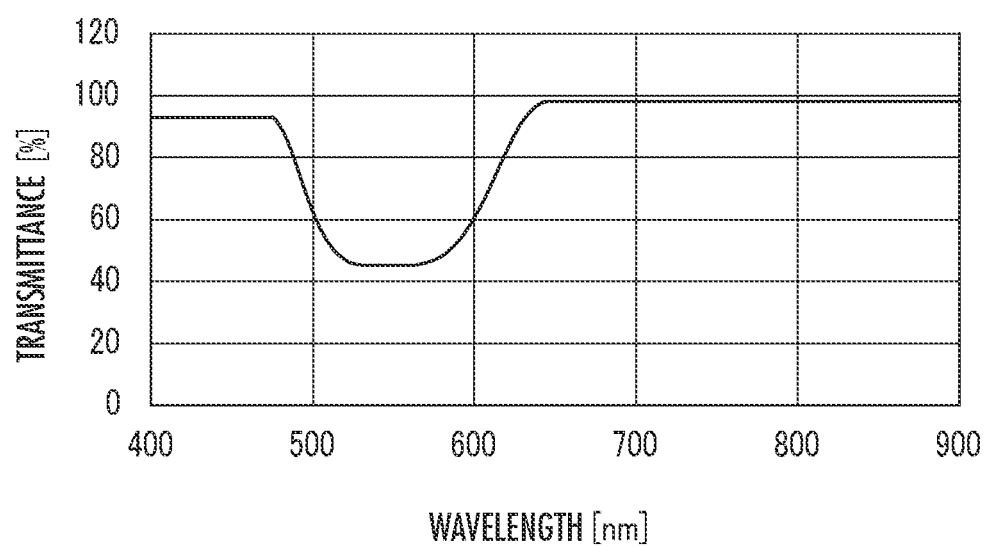
FIG. 4B is a diagram showing a relationship between a wavelength and a transmittance of the notch filter.

FIG. 4B is a diagram showing a relationship between the wavelength and the transmittance of the notch filter 38. The characteristics of the transmittance of the notch filter 38 have an attenuation region in which the transmittance is significantly reduced in a predetermined wavelength range (for example, approximately 500 nm to approximately 600 nm).

Figure 4C:
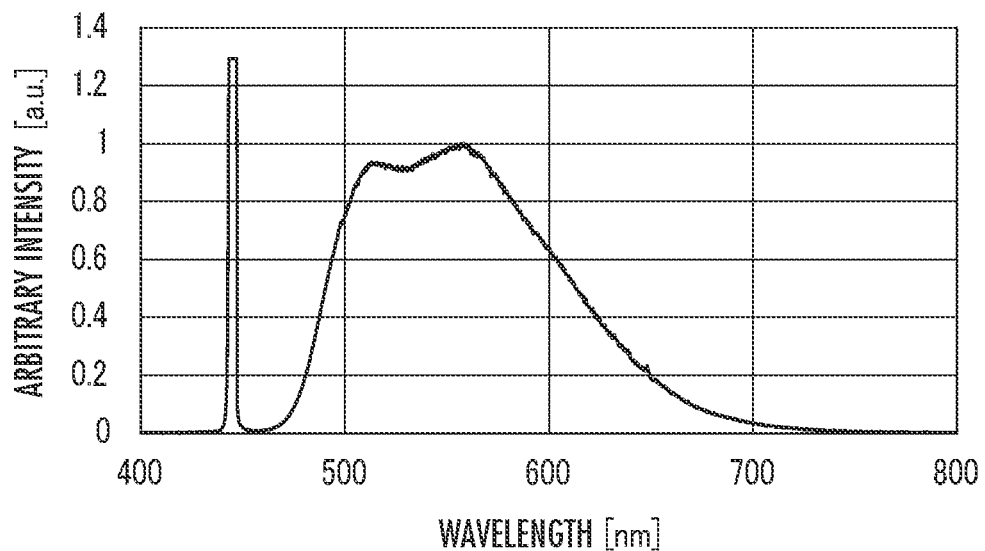
FIG. 4C is a diagram showing a relationship between a wavelength and an arbitrary intensity when laser light LDb during emission from a laser diode and primary fluorescence FL1 during emission from a fluorescent body are combined.

FIG. 4C is a diagram showing a relationship between a wavelength and an arbitrary intensity when the laser light LDb during emission from the laser diode 12 and the primary fluorescence FL1 during emission from the fluorescent body 18 are combined. An arbitrary intensity of the laser light LDb emitted from the laser diode 12 is concentrated in the vicinity of a wavelength $\lambda$ of 450 nm, and in FIG. 4C, an arbitrary intensity of the laser light LDb is in the vicinity of 1.3, but in reality, an arbitrary intensity is higher than 1.3 and cannot be entirely measured by a spectroscope and has a flat top due to saturation.

Figure 4D:
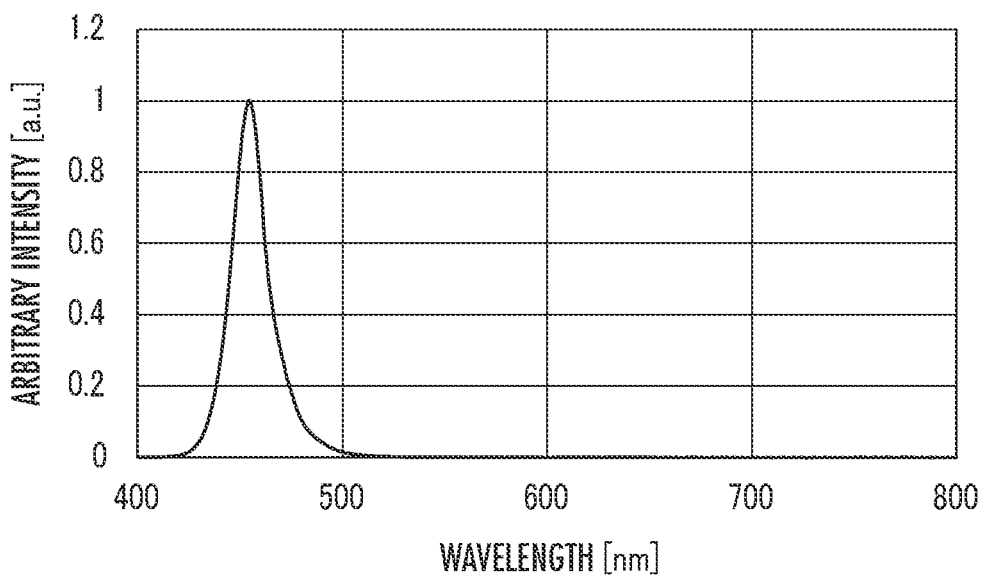
FIG. 4D is a diagram showing a relationship between a wavelength and an arbitrary intensity of LED light LEb emitted by an LED.

FIG. 4D is a diagram showing a relationship between the wavelength and an arbitrary intensity of LED light LEb emitted by the LED 30. FIG. 4E is a diagram showing a relationship between the wavelength and an arbitrary intensity of the laser light LDb emitted by the laser diode 12. The wavelengths $\lambda$ at which arbitrary intensities are the maximum are substantially the same between the LED light LEb and the laser light LDb, but it can be understood that a wavelength width in a case in which the intensities are half of the peak is wide and ensured in the LED light LEb, but is too narrow in the laser light LDb, and thus the minimum required intensity cannot be ensured in the wavelength range required for use in the imaging diagnosis with the fundus camera in a wavelength range of $\lambda 2$ or lower.

Returning to FIG. 3, the characteristics of the transmittance of the dichroic mirror 40 (two-dot chain line) and the characteristics of the transmittance of the notch filter 38 (one-dot chain line) are transcriptions in FIG. 3 of the characteristics of FIG. 4A and FIG. 4B, respectively. In the combined wave spectrum (solid line) of the secondary fluorescence FL2 as the emitted light of the dichroic mirror 40 and the LED light LEb, a wavelength range of $\lambda < \lambda 2$ with a wavelength $\lambda = \lambda 2$ as a border is a transcription of the characteristics in the same wavelength range in FIG. 4D, a wavelength range of λ>λ2 is obtained by multiplying the transmittance in FIG. 4B and an arbitrary intensity in FIG. 4C in the same wavelength range and converting the intensity of each wavelength in the wavelength range of λ>λ2 into an arbitrary intensity such that an actual intensity corresponding to the maximum multiplying value corresponds to the intensity corresponding to 1 as an arbitrary intensity of FIG. 4D, and is described in FIG. 3.

In FIG. 3, the intensities in both wavelength ranges of the combined wave spectrum are adjusted such that the maximum intensity in the wavelength range of λ<λ2 and the maximum intensity in the wavelength range of λ>λ2 are equal to each other. The characteristics of the notch filter 38 are set such that a condition of the intensity of the target value (upper broken line) or higher is satisfied and a condition of the intensity of the target value (lower broken line) or higher outside the wavelength range λ3-λ4 is satisfied.

(Action)

In FIG. 2, the laser diode 12 emits the laser light LDb. The laser light LDb has a wavelength lower than λ2 as blue coherent light, and has a higher intensity than the LED light LEb. The laser light LDb is converted into the primary fluorescence FL1 in association with passing through the fluorescent body 18. A wavelength of the primary fluorescence FL1 is λ2 or higher. Apart of the laser light LDb passes through the fluorescent body 18 as it is without being converted into the primary fluorescence FL1.

The primary fluorescence FL1 and the laser light LDb reach the notch filter 38. Transmission characteristics of the notch filter 38 are as shown by a one-dot chain line in FIG. 3. The notch filter 38 is disposed in an optical path of the primary fluorescence FL1 in a state of being inclined with a predetermined inclination angle. The laser light LDb having the wavelength lower than λ2 is transmitted straight through the notch filter 38 as it is.

In addition, the primary fluorescence FL1 having a wavelength of λ2 or higher is divided into the reflected fluorescence FLc as reflected light and the secondary fluorescence FL2 as transmitted light in the notch filter 38 in accordance with the transmission characteristics of the notch filter 38. An emission direction of the reflected fluorescence FLc from the notch filter 38 is a side opposite to the disposition side of the photodetector 24 with respect to the optical axis of the primary fluorescence FL1 in a predetermined vertical direction. The secondary fluorescence FL2 is emitted straight from the notch filter 38 together with the laser light LDb having the wavelength lower than λ2.

The secondary fluorescence FL2 corresponds to a spectrum line of λ2 or higher of the combined wave spectrum (solid line) of FIG. 3. In addition, the reflected fluorescence FLc changes a direction by 90° in the notch filter 38 and is reflected to a side opposite to the photodetector 24 with respect to the optical path of the primary fluorescence FL1. In other words, the reflected fluorescence FLc is reflected in a direction of turning away from the photodetector 24, preferably in a direction far away from the photodetector 24. As a result, the photodetector 24 prevents the reflected fluorescence FLc from being picked up and the incorrect detection of the light amount of the primary fluorescence FL1.

The secondary fluorescence FL2 and the laser light LDb that have passed through the notch filter 38 reach the dichroic mirror 40. The transmission characteristics of the dichroic mirror 40 are as shown by the two-dot chain line in FIG. 3. Since the laser light LDb is light having the wavelength lower than λ2, the laser light LDb is blocked from passing through the dichroic mirror 40 and is reflected in the same reflection direction as the reflected fluorescence FLc in a direction of 90° with respect to the optical axis on the incidence side. Since the secondary fluorescence FL2 is light having the wavelength of λ2 or higher, the secondary fluorescence FL2 is emitted straight through the dichroic mirror 40.

A surface of the dichroic mirror 40 on the emission side of the secondary fluorescence FL2 is also the incidence surface for the LED light LEb from the LED 30 at the same time. Since the LED light LEb is light having the wavelength lower than λ2, the LED light LEb changes a direction by 90° toward the collimator lens 44 in the dichroic mirror 40, is reflected, is combined with the secondary fluorescence FL2, and is emitted toward the collimator lens 44. The combined wave spectrum (solid line) of FIG. 3 indicates a relationship between the intensity and the wavelength of the combined light.

The light source driving device 50 controls the driving voltages of the laser diode 12 and the LED 30 based on the detection signals of the photodetectors 24 and 34 such that the intensity in the wavelength range λ3-λ4 (500 to 600 nm) to which the secondary fluorescence FL2 contributes and the maximum intensity (in the example of FIG. 3, the intensity of λ1) in the wavelength range of lower than λ2 (440 to 470 nm) to which the LED light LEb contributes are both equal to an arbitrary intensity 1, in the combined wave spectrum (solid line). Further, in this case, the transmission characteristics of the notch filter 38 and the dichroic mirror 40 are set such that an arbitrary intensity of the combined wave spectrum at λ2 is ensured to be equal to or higher than the lower target value.

Supplementary and Modification Example

The light source device 10 is used as a light source device for the imaging diagnosis with the fundus camera. The light source device according to the present invention can be applied as a light source device of an analysis device or an imaging device. The light source device 10 according to the present invention is configured as one light source module, but need not be configured as a module, or may be configured as an assembly of a plurality of modules.

The laser diode 12 and the LED 30 are examples of a laser light source and an LED light source according to the present invention, respectively. The laser light source and the LED light source according to the present invention may emit a color other than blue. In this case, set values of λ1 to λ4 are changed depending on an application state by those skilled in the art.

In the light source device 10, the optical paths of the laser light LDb and each light (primary fluorescence FL1 and secondary fluorescence FL2) derived from the laser light LDb extend straight, but may be appropriately bent depending on the application state of the light source device 10.

The wavelength λ2 of the light source device 10 corresponds to a first wavelength according to the present invention. In FIG. 3, the wavelength λ2 is set to the wavelength of the minimum intensity of the combined wave spectrum, but the first wavelength according to the present invention can also be set in a range of λ1<first wavelength<λ3.

The wavelength λ1 of the light source device 10 corresponds to a maximal intensity wavelength of an LED light according to the present invention. In the light source device 10, the maximal intensity wavelength of the LED light is only one, that is, λ1, and thus λ1 is also a wavelength of the maximum light amount of the LED light.

The photodetector 24 of the light source device 10 corresponds to a light sensor according to the present invention. Each optical axis in the light source device 10 is also an optical path of the corresponding light.

In the light source device 10, in the optical element 36, the notch filter 38 and the dichroic mirror 40 are formed by film-formation on one surface and the other surface of the glass substrate 39. In the present invention, a transparent substrate different from the glass substrate 39 can also be used as a transparent substrate coated with the notch filter and the dichroic mirror.

10: light source device
12: laser diode (laser light source)
18: fluorescent body
24: photodetector
30: LED (LED light source)
38: notch filter
39: glass substrate (transparent substrate)
40: dichroic mirror
LDb: laser light
LEb: LED light
FL1: primary fluorescence
FL2: secondary fluorescence
FLc: reflected fluorescence

What is claimed is:

1. A light source device comprising:
   a laser light source configured to emit laser light having a wavelength shorter than a first wavelength;
   a fluorescent body configured to emit primary fluorescence having a wavelength longer than the first wavelength by being excited by the laser light;
   a notch filter configured to emit secondary fluorescence obtained by attenuating the primary fluorescence from the fluorescent body in an attenuation wavelength range including a wavelength longer than the first wavelength;
   an LED light source configured to emit LED light having a wavelength shorter than the first wavelength; and
   a dichroic mirror configured to emit combined light obtained by combining the secondary fluorescence from the notch filter and the LED light from the LED light source.

2. The light source device according to claim 1, wherein the notch filter divides the primary fluorescence into the secondary fluorescence transmitted through the notch filter and reflected fluorescence reflected from the notch filter.

3. The light source device according to claim 2, further comprising:
   a light sensor configured to detect a light amount of the primary fluorescence in an optical path between the fluorescent body and the notch filter,
   wherein the notch filter is disposed in the optical path in a direction in which the reflected fluorescence is reflected in a direction of turning away from the light sensor.

4. The light source device according to claim 1, wherein the dichroic mirror allows the secondary fluorescence incident from the notch filter on one surface to travel straight and be emitted from the other surface, and reflects the LED light incident from the LED light source on the other surface in a same direction as an emission direction of the secondary fluorescence.

5. The light source device according to claim 1, wherein the notch filter and the dichroic mirror are respectively film-formed on one surface and the other surface of a same transparent substrate.

6. The light source device according to claim 1, wherein a maximum light amount of the secondary fluorescence and a maximum light amount of the LED light are equal to each other in the combined light.

* * * * *